United States Patent [19]

Quinlan

[11] 4,312,830

[45] Jan. 26, 1982

[54] TERTIARY AMINO-SUBSTITUTED THIAZINES

[75] Inventor: Patrick M. Quinlan, Webster Groves, Mo.

[73] Assignee: Petrolite Corporation, St. Louis, Mo.

[21] Appl. No.: 161,989

[22] Filed: Jun. 23, 1980

Related U.S. Application Data

[62] Division of Ser. No. 713,706, Aug. 12, 1976, Pat. No. 4,263,433.

[51] Int. Cl.$^3$ .................... C23F 11/14; C23F 11/16
[52] U.S. Cl. ........................... 422/12; 252/391; 252/8.55 E; 422/7; 422/16; 544/58.2
[58] Field of Search ............... 252/391, 8.55 E; 422/7, 422/12, 16; 544/58, 58.2

[56] References Cited

U.S. PATENT DOCUMENTS

| | | | |
|---|---|---|---|
| 2,483,671 | 10/1949 | Rieveschl | 544/59 |
| 2,675,381 | 4/1954 | Craig et al. | 252/390 |
| 2,752,343 | 6/1956 | Fegley et al. | 544/78 |
| 3,828,036 | 8/1974 | Quinlan | 544/58 |
| 3,946,008 | 3/1976 | Brown et al. | 544/60 |
| 3,983,110 | 9/1976 | Brown et al. | 544/60 |
| 4,146,711 | 3/1979 | Quinlan | 252/391 |
| 4,188,359 | 2/1980 | Quinlan | 252/391 |
| 4,217,329 | 8/1980 | Quinlan | 252/391 |

*Primary Examiner*—Benjamin R. Padgett
*Assistant Examiner*—Irwin Gluck
*Attorney, Agent, or Firm*—Sidney B. Ring; Hyman F. Glass

[57] ABSTRACT

This invention relates to tertiary amino-substituted thiazines; the process of preparing such thiazines; and uses thereof, for example, as corrosion inhibitors, microbiocides, etc.

9 Claims, No Drawings

TERTIARY AMINO-SUBSTITUTED THIAZINES

This Application is a division of Ser. No. 713,706, filed Aug. 12, 1976 by Patrick M. Quinlan now U.S. Pat. No. 4,263,433.

This invention relates to tertiary aminosubstituted thiazines such as 4-(tertiary-aminoalkylene) substituted 1,4-thiazines of the formulae:

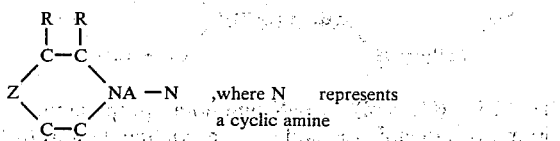, where N represents a cyclic amine

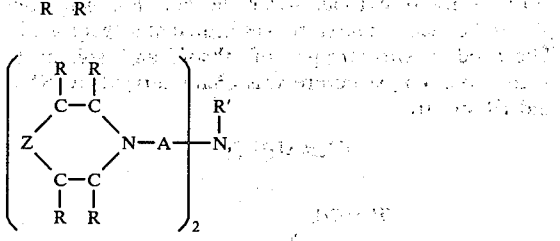

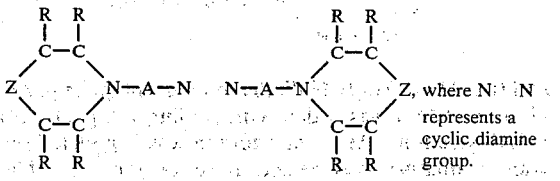, where N N represents a cyclic diamine group.

where the R's are hydrogen or a substituted group such as a hydrocarbon group, i.e., alkyl, etc.; and R' is a hydrocarbon group such as alkyl, or a substituted alkyl such as hydroxyalkyl and the like; Z is S, SO, SO$_2$; and A is alkylene, alkenylene, alkinylene, etc.

When divinyl sulfone is treated with a primary amine, derivatives of 1,4-thiazine -1,1-dioxide result. The compounds of this invention are prepared by reacting a divinyl sulfur compound with an organic compound containing one or more primary and tertiary amino groups. The reaction of a compound containing one primary and one tertiary amino group such as N,N dimethyl-1,3-propanediamine may be illustrated by the following general equation:

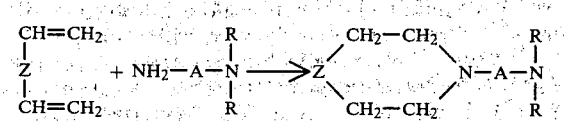

where A is alkylene such as (CH$_2$)$_{2-10}$ or greater and the R's are hydrocarbon such as alkyl, substituted alkyl, etc.

In addition one mol of an alkylimino bis-alkylamine having two primary amino groups and one tertiary amino group such as methyliminobispropylamine or an N,N'-bis (aminoalkylene)-di-tertiary amine such as N,N'bis(3-aminopropyl)-piperazine having two primary amino groups and two tertiary amino groups reacts with two mols of a divinyl sulfur compound in a similar manner.

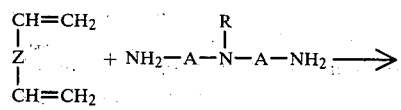

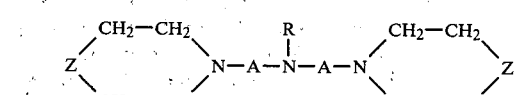

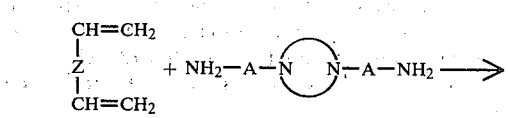

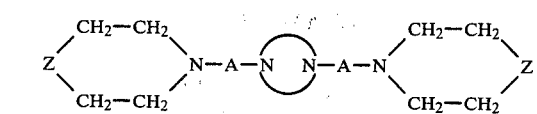

N N represents a cyclic diamine

The amine which reacts with the divinyl sulfur compound contains at least one primary amino group and at least one tertiary amino group. Thus, it may contain one primary and one tertiary amino group, e.g.,

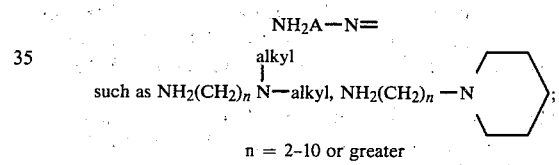

n = 2-10 or greater one tertiary amino group and two primary amino groups such as

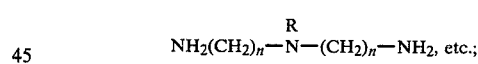

two tertiary and two primary amino groups such as

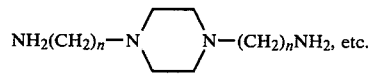

In the resulting product the primary amino group or groups become part of the thiazine ring while the tertiary amino group remains unchanged. Thus, the final product contains one or two thiazine groups and one or two tertiary amino groups.

Examples of the divinyl sulfur compounds are:

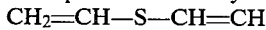

Examples of compounds having one primary amino group and one tertiary amino group include N,N-dimethyl propanediamine, N,N-diethylpropanediamine, N,N-diethylethylenediamine, N-(3-aminopropyl) diethanolamine, N-(3-piperidino) propylamine, N-(3-aminopropyl) morpholine and the like.

An example of a compound having two primary amino groups and two tertiary amino groups is N,N'-Bis(3-aminopropyl)piperazine.

In carrying out the reaction the divinyl sulfone is usually added to an alcoholic solution of the amine. However any non-reactive solvent may be employed. In some cases the amine is added to an alcoholic solution of the divinyl sulfone particularly when a plurality of primary amino groups is present. The reaction is exothermic and cooling is usually employed to moderate the heat of reaction. A reaction temperature of between 25° and 60° C. is preferred. After addition a short period of reflux may be employed to ensure complete reaction. The reaction product may be isolated and purified by employing conventional techniques. The yields of the desired products are quite excellent.

The invention may be illustrated by the following examples.

EXAMPLE 1

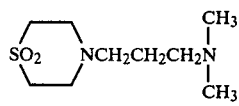

To 102 g. (1 mol) of N,N-dimethyl 1,3-propanediamine dissolved in 150 ml. of methanol was slowly added, with external cooling, 118 g. (1 mole) of divinyl sulfone. After the addition had been completed, the mixture was heated at reflux for 1 hour. The methanol was stripped off, using a rotary evaporator, leaving a viscous liquid product. The product was distilled in vacuo. The main portion had a B.P. of 170–172/2 mm. Recovered 176 g. of a yellow viscous liquid (80% of theory)

Analyses-Calculated for $C_9H_{20}N_2O_2S$ (percent): N, 12.75; S, 14.54: Found (percent): N, 12.78; S, 14.37.

IR and NMR spectra were used to characterize and verify the above structure.

EXAMPLE 2

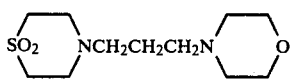

118 g. (1 mol) of divinylsulfone was added with cooling to a solution of 144.2 g. (1 mol) of N-aminopropyl morpholine in 350 ml. of methanol. After the addition had been completed, the solution was heated at reflux for 1 hr. Methanol was removed leaving a viscous liquid that crystallized upon standing. The crude product was recrystallized from ethanol.

Analyses:-Calculated for $C_{11}H_{22}N_2O_3S$: N, 10.69; S, 12.21. Found: N, 10.46; S, 11.86.

EXAMPLE 3

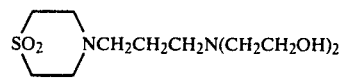

162 g. (1 mol) of N-(3-aminopropyl) diethanolamine was dissolved in 300 ml. of methanol. To this solution was slowly added with cooling 118 g. (1 mol) of divinyl sulfone. The crude product was isolated and purified by distillation.

EXAMPLE 4

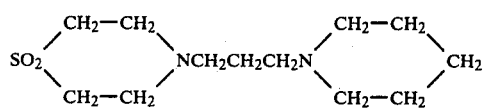

To 12.8 g (0.1 mol) of 3-(N-piperidino)propylamine in 50 ml. of ethanol was added with cooling 11.8 g. (0.1 mol) of divinylsulfone. After the addition was completed the reaction mixture was heated at reflux for 1 hr. The product was stripped of ethanol and isolated by distillation. The structure was characterized by NMR and IR spectra.

EXAMPLE 5

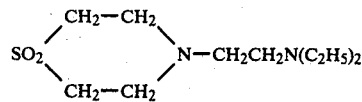

To 116 g. (1 mol) of N,N-diethyl ethylenediamine in 350 ml. of methanol was added with cooling 118 g. (1 mol) of divinylsulfone. After the addition was completed the reaction mixture was heated at reflux for 1 hr. The product was stripped of methanol and isolated by distillation

EXAMPLE 6

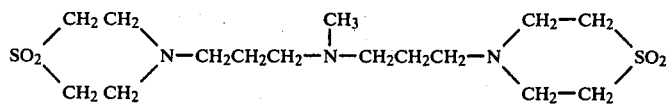

To 236.05 g. (2 mol) of divinylsulfone dissolved in 350 ml. of 2-propanol was slowly added with cooling 145.0 g. (1 mol) of methyliminobispropylamine. After the addition had been completed, the reaction mixture was heated at reflux for 1 hour. The 2-propanol was removed on a rotary evaporator and the crude liquid product crystallized upon standing. It was recrystallized from ethanol.

Analyses:—Calculated for $C_{15}H_{31}N_3O_4S_2$: N, 9.07; S, 16.80. Found - N, 9.00; S, 16.72.

The above structure was characterized by NMR and IR spectra.

EXAMPLE 7

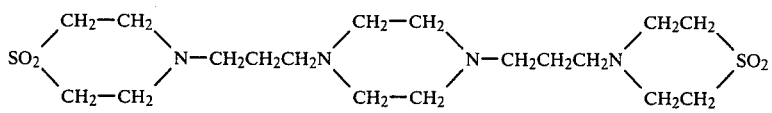

To 100 g. (0.5 mol) of N,N'-Bis(3-aminopropyl) piperazine dissolved in 200 ml. of 2-propanol was slowly added with cooling 118 g. (1 mol) of divinylsulfone. After the addition had been completed, the reaction mixture was heated at reflux for 1 hr. The 2-propanol was removed using a rotary evaporator leaving a white powder. The solid was purified by washing with acetone and recrystallized from a mixture of benzene and petroleum ether.

Analyses-Calculated for $C_{18}H_{36}N_4O_4S_2$: N, 12.84; S, 14.68. Found-N, 12.74; S, 14.73.

USES

This invention also relates to the inhibition of corrosion, particularly the corrosion of metals in contact with the acid solutions.

The present invention is especially useful in the acidizing or treating of earth formations and wells traversed by a bore hole. It may also be used in metal cleaning and pickling baths which generally comprise aqueous solutions of inorganic acids such as sulfuric acid, hydrochloric acid, phosphoric acid and are useful in the cleaning and treatment of iron, zinc, ferrous alloys, and the like.

If no corrosion inhibitor is present when the aqueous acidic solution comes in contact with the metal, excessive metal loss and consumption or loss of acid, and other adverse results will be experienced. There has been a continuing search for corrosion inhibitors which can be used effectively in small concentrations, and which are economical to produce. The need is also for corrosion inhibitors which are effective at high temperatures, e.g., 200° F. and above, such as are found in operations involving acidic solutions, particularly oil-well acidizing where higher and higher temperatures are found as the well extends further into the earth.

While the compounds of this invention are of themselves particularly good acid corrosion inhibitors, optionally they may be blended with acetylenic alcohols, dispersing and solubilizing agents such as ethoxylated phenols, alcohols, and fatty acids. They may also be blended with such known acid inhibitors as the quinoline or alkyl pyridine quaternary compounds or synergists such as terpene alcohols, formamide, formic acid, alkyl amine, alkylene polyamines, heterocyclic amines, and the like.

USE IN ACID SYSTEMS

The compounds of this invention can also be employed as corrosion inhibitors for acidic systems, for example as illustrated by the pickling of ferrous metals, the treatment of calcareous earth formations, etc., as described in the following sections.

USE IN ACIDIZING EARTH FORMATIONS

The compositions of this invention can also be used as corrosion inhibitors in acidizing media employed in the treatment of deep wells to reverse the production of petroleum or gas therefrom and more particularly to an improved method of acidizing a calcareous or magnesium oil-bearing formation.

It is well known that production of petroleum or gas from a limestone, dolomite, or other calcareousmagnesian formation can be stimulated by introducing an acid into the producing well and forcing it into the oil or gas bearing formation. The treating acid, commonly a mineral acid such as HCl, is capable of forming water soluble salts upon contact with the formation and is effective to increase the permeability thereof and augment the flow of petroleum to the producing well.

CORROSION TEST PROCEDURE

In these tests the acid solutions were mixed by diluting concentrated hydrochloric acid with water to the desired concentrations.

Corrosion coupons of ASTM N-80 steel were pickled in an uninhibited 10% HCL solution for 10 minutes, neutralized in a 10% solution of $NaHCO_3$, dipped in acetone to remove water and allowed to dry. They were then weighed to the nearest milligram and stored in a desiccator.

In all of the tests, a 25 $cc/in^2$ acid volume to coupon surface area ratio was used. After the desired amount of acid was poured into glass bottles, the inhibitor was added. The inhibited acid solution was then placed in a water bath which had been set at a predetermined temperature and allowed to preheat for 20 minutes. After which time the coupons were placed in the preheated inhibited acid solutions. The coupons were left in the acid solution for the specified test time, then removed, neutralized, rinsed, dipped in acetone, allowed to dry, and then reweighed.

The loss in weight in grams was multiplied times a calculated factor to convert the loss in weight to $lbs/ft^2/24$ hrs.

The factor was calculated as follows:

$$\frac{\frac{144 \text{ in}^2}{\text{ft}^2}}{\frac{454 \text{ g}}{\text{lb}} \times \text{coupon surface area (in}^2) \times \frac{1 \text{ day}}{24 \text{ hrs.}}} = \text{Factor}$$

TABLE 1

Acid Corrosion Test

| Inhibitor | conc. in ppm | Test Temp. (°F.) | Duration of test (Hrs.) | Corrodent | Coupon Metal Type | Corrosion Rate (lbs/ft²/day) |
|---|---|---|---|---|---|---|
| Ex. 2 | 2000 | 150 | 6 | 15% HCl | N-80 | 0.0427 |
| 4 | 2000 | 150 | 6 | 15% HCl | N-80 | 0.0511 |
| 6 | 2000 | 150 | 6 | 15% HCl | N-80 | 0.0499 |
| 7 | 2000 | 150 | 6 | 15% HCl | N-80 | 0.0474 |
| Blank | — | 150 | 6 | 15% HCl | N-80 | 0.1956 |

USE IN BRINES

This phase of the invention relates to the prevention of corrosion in systems containing a corrosive aqueous medium, and most particularly in systems containing brines.

More particularly, this invention relates to the prevention of corrosion in the secondary recovery of petroleum by water flooding and in the disposal of waste water and brine from oil and gas wells. Still more particularly, this invention relates to a process of preventing corrosion in water flooding and in the disposal of waste water and brine from oil and gas wells which is characterized by injecting into an underground formation an aqueous solution containing minor amounts of compositions of this invention, in sufficient amounts to prevent the corrosion of metals employed in such operation. This invention also relates to corrosion inhibited brine solutions of these compounds.

When an oil well ceases to flow by the natural pressure in the formation and/or substantial quantities of oil can no longer be obtained by the usual pumping methods, various processes are sometimes used for the treatment of the oil-bearing formation in order to increase the flow of the oil. These processes are usually described as secondary recovery processes. One such process which is used quite frequently is the water flooding process wherein water is pumped under pressure into what is called an "injection well" and oil, along with quantities of water, that have been displaced from the formation, are pumped out of an adjacent well usually referred to as a "producing well". The oil which is pumped from the producing well is then separated from the water that has been pumped from the producing well and the water is pumped to a storage reservoir from which it can again be pumped into the injection well. Supplementary water from other sources may also be used in conjunction with the produced water. When the storage reservoir is open to the atmosphere and the oil is subject to aeration this type of water flooding system is referred to herein as an "open water flooding system." If the water is recirculated in a closed system without substantial aeration, the secondary recovery method is referred to herein as a "closed water flooding system."

Because of the corrosive nature of oil field brines, to economically produce oil by water flooding, it is necessary to prevent or reduce corrosion since corrosion increases the cost thereof by making it necessary to repair and replace such equipment at frequent intervals.

I have now discovered a method of preventing corrosion in systems containing a corrosive aqueous media, and most particularly in systems containing brines, which is characterized by employing the compositions of this invention.

I have also discovered an improved process of protecting from corrosion metallic equipment employed in secondary oil recovery by water flooding such as injection wells, transmission lines, filters, meters, storage tanks, and other metallic implements employed therein and particularly those containing iron, steel, and ferrous alloys, such process being characterized by employing in water flood operation the compositions of this invention.

This phase of the invention then is particularly concerned with preventing corrosion in a water flooding process characterized by the flooding medium containing an aqueous or an oil field brine solution of these compounds.

In many oil fields large volumes of water are produced and must be disposed of where water flooding operations are not in use or where water flooding operations cannot handle the amount of produced water. Most States have laws restricting pollution of streams and land with produced waters, and oil producers must then find some method of disposing of the waste produced salt water. In many instances, therefore, the salt water is disposed of by injecting the water into permeable low pressure strata below the fresh water level. The formation into which the water is injected is not the oil producing formation and this type of disposal is defined as salt water disposal or waste water disposal. The problems of corrosion of equipment are analagous to those encountered in the secondary recovery operation by water flooding.

The compositions of this invention can also be used in such water disposal wells thus providing a simple and economical method of solving the corrosion problems encountered in disposing of unwanted water.

Water flood and waste disposal operations are too well know to require further elaboration. In essence, in the present process, the flooding operation is effected in the conventional manner except that the flooding medium contains a minor amount of the compound of this invention, sufficient to prevent corrosion, in concentrations of about 10 ppm to 10,000 ppm., or more, for example, about 50 to 5,000 ppm., but preferably about 15 to 1,500 ppm. The upper limiting amount of the compounds is determined by economic considerations. Since the success of a water flooding operation manifestly depends upon its total cost being less than the value of the additional oil recovered from the oil reservoir, it is quite important to use as little as possible of these compounds consistent with optimum corrosion inhibition. Optimum performance is generally obtained employing about 1,000 ppm. Since these compounds are themselves inexpensive and are used in low concentrations, they enhance the success of a flood operation by lowering the cost thereof.

In addition, these compounds are not sensitive to oxygen content of the water and these are effective corrosion inhibitors in both open water flooding systems and closed water flooding systems.

While the flooding medium employed in accordance with the present invention contains water or oil field brine and the compounds, the medium may also contain other materials. For example, the flooding medium may also contain other agents such as surface active agents or detergents which aid in wetting throughout the system and also promote the desorption of residual oil from the formation, sequestering agents which prevent the deposition of calcium and/or magnesium compounds in the interstices of the formation, bactericides which prevent the formation from becoming plugged through bacterial growth, tracers, etc. Similarly, they may be employed in conjunction with any of the operating techniques commonly employed in water flooding and water disposal processes, for example five spot flooding, peripheral flooding, etc., and in conjunction with other secondary recovery methods.

Static weight loss tests—These tests are run on both synthetic and naturally occurring fluids. The test procedure involves the measurement of the corrosive action of the fluids inhibited by the compositions herein described upon sandblasted S.A.E. 1020 steel coupons measuring $\frac{7}{8} \times 3\frac{1}{4}$ inches under conditions approximating those found in an actual producing well, and the comparison thereof with results obtained by subjecting identical test coupons to the corrosive action of identical fluids containing no inhibitor.

Clean pint bottles were charged with 200 ml. of 10% sodium chloride solution saturated with hydrogen sulfide and 200 ml. of mineral spirits and a predetermined amount of inhibitor was then added. In all cases the inhibitor concentration was based on the total volume of the fluid. Weighed coupons were then added, the bottles tightly sealed and allowed to remain at room temperature for 3 days. The coupons were then removed, cleansed by immersion in inhibited 10% HCl, dried and weighed.

The changes in the weight of the coupons during the corrosion test were taken as a measurement of the effectiveness of the inhibitor compositions. Protection percentage was calculated for each test coupon taken from the inhibited fluids in accordance with the following formula:

$$\frac{L_1 - L_2}{L_1} \times 100 = \% \text{ Protection}$$

in which $L_1$ is the loss in weight of the coupons taken from inhibited fluids and $L_2$ is the loss in weight of coupons which were subjected to the inhibited fluids.

TABLE 2

| Static Weight Loss Test | | |
|---|---|---|
| Example | ppm | % Protection |
| 1 | 1000 | 85.4 |
| 2 | 1000 | 82.6 |
| 3 | 1000 | 78.3 |
| 4 | 1000 | 77.4 |
| 5 | 1000 | 73.2 |
| 6 | 1000 | 74.1 |
| 7 | 1000 | 76.7 |

USE AS MICROBIOCIDE

Microbiocidal testing

The screening procedure was as follows: a 1.0% by weight solution of the test compound in water was prepared. The solution was aseptically added to a sterile broth that would support the growth of the test organism, Desulfofivbrid desulfuricans, to provide a concentration of 25 to 100 parts by weight of test compound per million parts by weight of broth. A general growth medium, such as prescribed by the American Petroleum Institute was used. The broth containing the test compound then was dispersed in 5 cc. amounts into sterile disposable tubes and the tubes were inoculated with the growing test organism and incubated at 35° C. for 36 hrs. The absence or presence of growth of the microorganisms was determined by visual inspection by an experienced observer. Following is a summary of the results of the testing of examples of this invention.

TABLE 3

| Microbiocidal Tests | |
|---|---|
| Compound | Concentration of test compound ppm |
| Ex. 1 | 100 |
| Ex. 2 | 50 |
| Ex. 4 | 50 |
| Ex. 6 | 75 |
| Ex. 7 | 50 |

In all of the above tests no growth of the test organism occurred, thus indicating that the compound is a biostatic or a biocide.

The amount of composition employed as corrosion inhibitor or microbiocide can vary widely depending on many variables such as the particular composition employed, the particular system, the particular corrodant or microorganism, etc. In general, one employs from about 1 to 10,000 ppm or more, such as from about 10–5,000 ppm, for example from about 50 to 2,500 ppm, but preferably 100–1,000 ppm.

I claim:

1. The process of inhibiting corrosion which comprises treating a system with a tertiary amino-substituted thiazine having the formula selected from the group consisting of

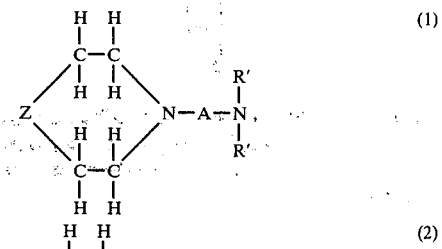

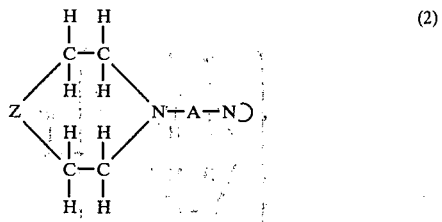

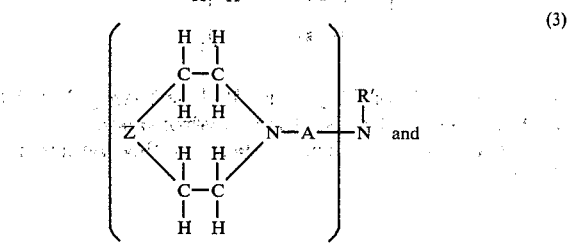

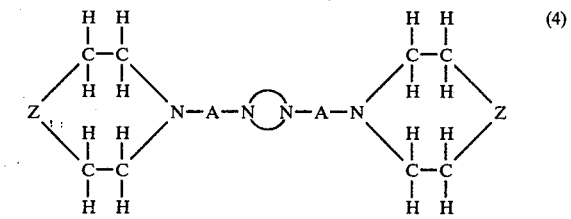

where Z is SO or $SO_2$, A is alkylene having 2 to 10 carbon atoms, R' is alkyl or hydroxyalkyl, $N\supset$ represents a cyclic amine group and

represents a cyclic diamine group.

2. The process of claim 1 where the thiazine has the formula

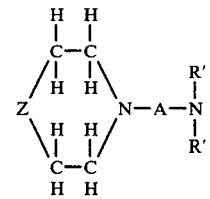

where Z is SO or $SO_2$, A is alkylene having 2 to 10 carbon atoms and R' is alkyl or hydroxyalkyl.

3. The process of claim 1 where the thiazine has the formula

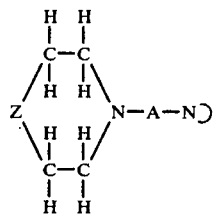

where Z is SO or SO$_2$, A is alkylene having 2 to 10 carbon atoms, and N represents a cyclic amine.

4. The process of claim 1 where the thiazine has the formula

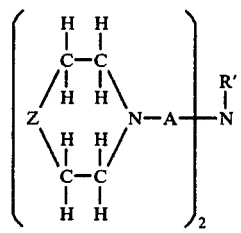

where Z is SO or SO$_2$, A is alkylene having 2 to 10 carbon atoms and R' is alkyl or hydroxyalkyl.

5. The process of claim 1 where the thiazine has the formula

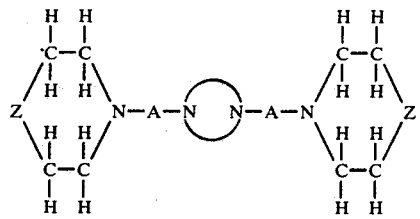

where Z is SO or SO$_2$ and A is alkylene having 2 to 10 carbon atoms.

6. The process of claim 1 where the thiazine has the formula.

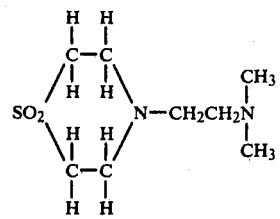

7. The process of claim 1 where the thiazine has the formula.

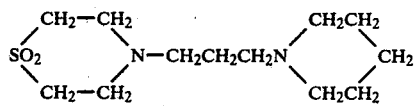

8. The process of claim 1 where the thiazine has the formula.

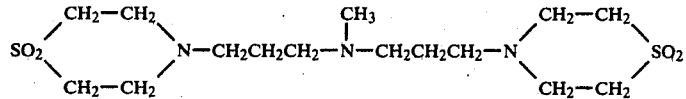

9. The process of claim 1 where the thiazine has the formula.

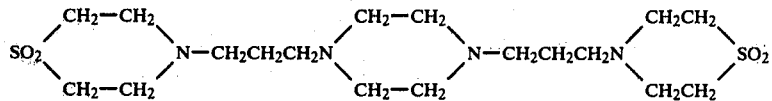

* * * * *